United States Patent [19]

Grassi

[11] Patent Number: 4,624,265
[45] Date of Patent: Nov. 25, 1986

[54] ELECTRO-CATHETER USED IN PHYSIOLOGICAL CARDIAC STIMULATION SIMULATIVE OF THE AURICULO-VENTRICULAR SEQUENCE, FEATURING ACTIVE ENGAGEMENT OF THE CARDIAC MUSCLE

[75] Inventor: Gino Grassi, Sesto Fiorentino (Fi), Italy

[73] Assignee: GE. SV. IN. S.R.I., Italy

[21] Appl. No.: 758,518

[22] Filed: Jul. 24, 1985

[51] Int. Cl.⁴ ............................................. A61N 1/04
[52] U.S. Cl. ..................................... 128/784; 128/786
[58] Field of Search ..................... 128/419 P, 642, 785, 128/786

[56] References Cited

U.S. PATENT DOCUMENTS 3,729,008  4/1973  Berkovits .................. 128/419 P
4,146,036  3/1979  Dutcher et al. ................ 128/785
4,233,992  11/1980 Bisping ............................. 128/785
4,357,946  11/1982 Dutcher et al. ............... 128/419 P
4,497,326  2/1985  Curry ............................... 128/785

FOREIGN PATENT DOCUMENTS 1523263  8/1978  United Kingdom ............... 128/642

Primary Examiner—Kyle L. Howell
Assistant Examiner—Randy Citrin
Attorney, Agent, or Firm—Darby & Darby

[57] ABSTRACT

The one-piece electro-catheter disclosed is intended for use with artificial pacemakers which reproduce the auriculo-ventricular rhythmic sequence (normally defined as 'physiological'). An electrocatheter according to the invention affords highly dependable contact with the cardiac muscle, being anchored thereto by an active type of mechanism in each one of the auricular and ventricular chambers. The implanted electrodes thus permit sensing and stimulation in both of the chambers, and there is the added advantage of having only one catheter to insert.

6 Claims, 6 Drawing Figures

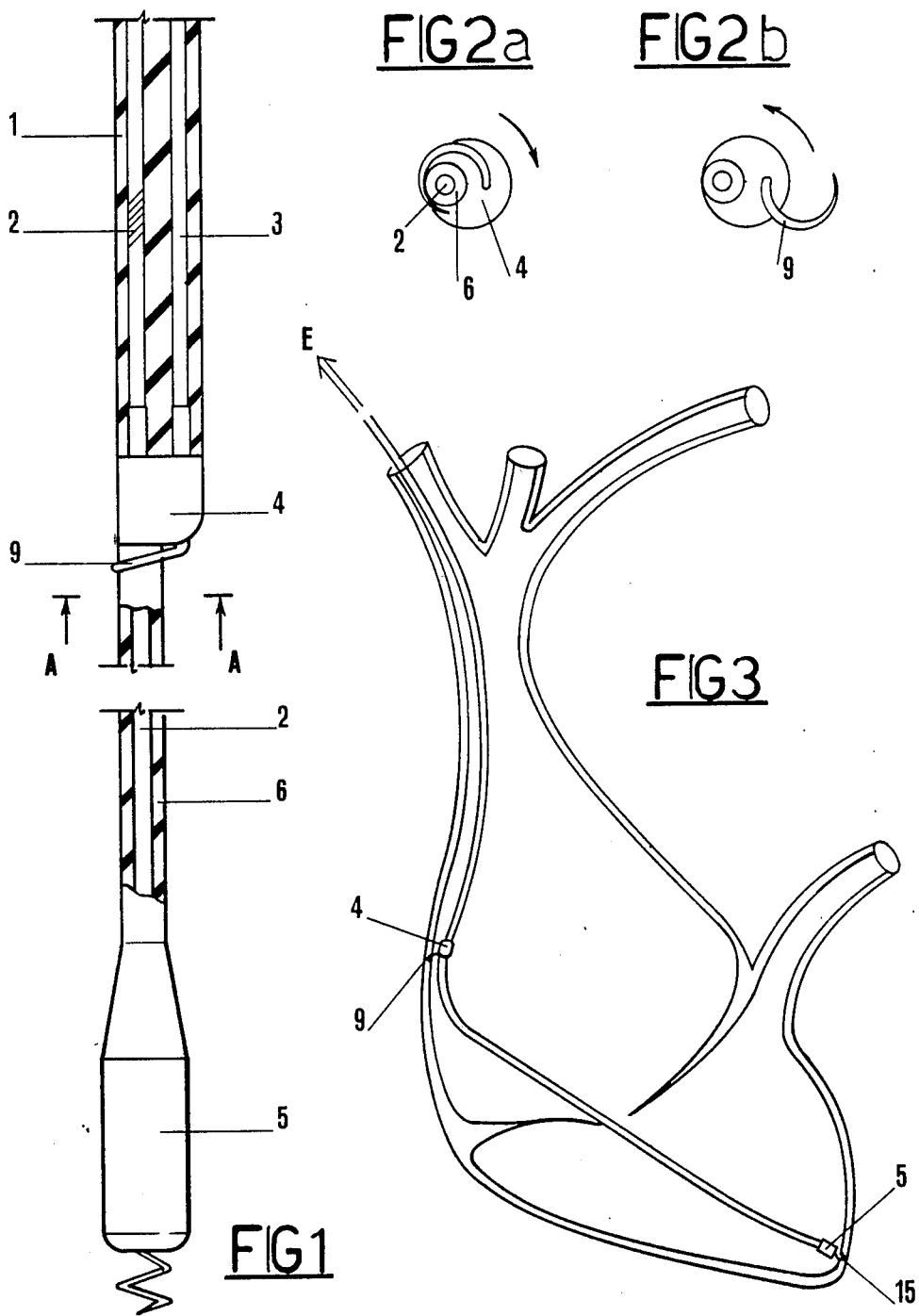

ELECTRO-CATHETER USED IN PHYSIOLOGICAL CARDIAC STIMULATION SIMULATIVE OF THE AURICULO-VENTRICULAR SEQUENCE, FEATURING ACTIVE ENGAGEMENT OF THE CARDIAC MUSCLE

BACKGROUND OF THE INVENTION

The invention relates to a one-piece electro-cathether with two independent and actively-engaging electrodes.

In the clinical practice of permanent cardiac stimulation (artificial pacemaker implantation), which is designed to prevent auriculo-ventricular and sinoatrial block, and in other connected types of therapy (treatment of sinoatrial node diseases, of brady/tachy-syndromes, and of hypo- and hyper-kinetic arrhythmia) there is an increasing trend toward so-called 'physiological' stimulation whereby it is sought to reproduce the natural auriculo-ventricular sequence, and to reconstruct the correct hemodynamic sequence, and, in cases where atrial activity still continues, to maintain the state of dependence on such metabolic signals as influence the pacemaking activity of the sinoatrial node.

To this end, use is made of a stimulator capable of receiving and acknowledging an electrical atrial depolarization signal by way of an electrode implanted in the atrium; the signal is amplified and exploited for the purpose of synchronizing a pulse generator which, following a preset delay calculated to match physiological parameters (100 to 200 msec), emits an electrical impulse such as will stimulate the ventricle by way of an electrode implanted therein; thus one reconstructs the natural auriculo-ventricular contractile sequence.

In the event of there being no atrial signal, or that the frequency available is lower than will match the sensitivity of the stimulator, a second pulse generator is utilized to stimulate the atrium by way of an electrode implanted therein, in the same way as for the ventricle, so as to maintain the physiological auriculo-ventricular sequence.

The use of such methods in practice has been significantly restricted thus far by the need for insertion of two catheter electrodes, one in the ventricle, the other in the atrium; this operation is rendered problematic by reason, amongst other considerations, of the smoothness of the inner wall of the chamber and the attendant difficulties of firm anchorage and stable contact.

The object of the invention is to prevent the difficulties thus outlined by adoption of a single catheter incorporating two independent electrodes.

SUMMARY OF THE INVENTION

The object thus stated is realized with a one-piece catheter as disclosed herein, the two independent electrodes of which are insulated, and arranged such that the one (proximal) is located in the atrium, and the other (distal) is located in the ventricle, the catheter itself being cylindrical in shape and having a distal extremity that incorporates the ventricular electrode, an actively engaging type with a spiral metal anchor (normally platinum-iridium alloy) which may be fixed or retractable.

The spiral, normally of 1 to 3 turns, serves to anchor the electrode; rotating the electrode, or the relative stylet, the anchor corkscrews into the cardiac muscle, drawing it into electrical contact with the cylindrical tip of the electrode.

A conductive cylindrical body, located along the cylindrical body of the catheter at a relative distance of between 10 and 18 cm (4–7 ins), performs the function of atrial electrode. A spiral hook with a sharp end issuing from this cylindrical body can be rotated through approximately 270° by means of a relative stylet. In a stowed position, the spiral hook wraps around the cylindrical conductor which extends into the ventricle, and lies with its axis of rotation parallel thereto.

The catheter can thus be introduced without the spiral hook penetrating the wall of the cardiac vein, and positioned in such a way that sensitivity and stimulus thresholds are acceptable for operation of the pacemaker, following which the spiral hook is rotated in such a way as to open out toward the wall of the heart, then rotated in the opposite direction so that its sharp point engages and sinks into the cardiac muscle, drawing the cylindrical body of the electrode into close contact therewith.

The electrical contact and mechanical fixture obtained in this way are produced by the simplest of maneuvers, and afford maximum dependability.

Advantages of the invention are essentially (1) that one electro-catheter only is introduced, permitting use of one vena cava only;

(2) that the ventricular and auricular electrodes are both made fast mechanically to the ventricle and atrium walls, ensuring efficient electrical contact at the same time, thereby reducing the percentage of removals and subsequent repositioning operations by at least 80%;

(3) that the catheter can be implanted utilizing the same surgery technique as is normally adopted for ordinary discrete catheter electrodes.

BRIEF DESCRIPTION OF THE DRAWINGS

An embodiment of the invention will now be described in detail, by way of example, with the aid of the accompanying drawings, in which:

FIG. 1 is a longitudinal view of an electro-catheter according to the invention, seen partly in section, showing the auricular electrode in a stowed position adopted during introduction, and showing the ventricular electrode with spiral anchor fully exposed;

FIG. 2a is a section through A—A in FIG. 1, showing the spiral hook in stowed position;

FIG. 2b is the same section through A—A, showing the spiral hook opened out into the engaging position;

FIG. 3 is a schematic representation of the location of an electro-catheter as disclosed, in the right auriculo and ventricular chambers of the heart;

DESCRIPTION OF THE PREFERRED EMBODIMENT

Figure 4:
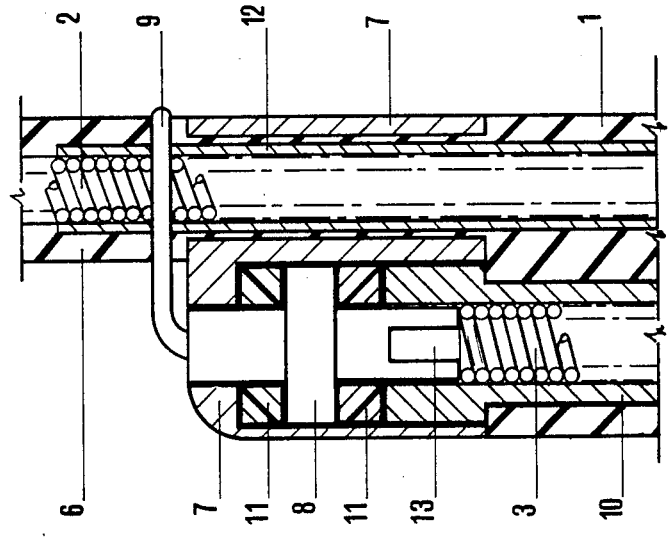
FIGS. 4 and 5 are detailed longitudinal sections through the ventricular and auricular electrodes, respectively.

With reference to the drawings, the electro-catheter consists essentially of a flexible insulating sheath 1 which is cylindrical in section and embodied in biocompatible material (e.g. silicon or polyurethane rubber), and has two axially-oriented and parallel cylindrical bores which accommodate two respective spiral-wound conductors 2 and 3.

The conductor denoted 2 extends beyond the body of the atrial electrode 4 to the ventricular electrode 5 (illustrated in detail in FIG. 4) and is carried thereto by a sheath 6 of smaller section than the dual-core sheath 1, designed as it is to accommodate and insulate one conductor only.

The conductor denoted 3 terminates at the auricular electrode 4 (illustrated in FIG. 5) to which it is ultimately connected.

The two conductors 2 and 3 are composed of one or more strands of a material possessing high, long-term tensile and torsional strength (Elgiloy MP35N for instance), and are spiral-wound about parallel axes in order to admit of running a stylet of straightened stainless steel wire through each of the two bores thus created. The stylet M, which is illustrated in broken line in FIG. 4, constitutes a separate accessory the distal extremity of which is embodied with parallel faces, or at any rate, in the form of a key which will register with a corresponding socket 13 or 18 offered by a moving part of the relative electrode 4 or 5, shortly to be described.

In addition to imparting rotational movement to the active electrode anchor, the stylet serves to guide the electro-catheter during its insertion and location into and within the cardiac chambers.

Figure 5:
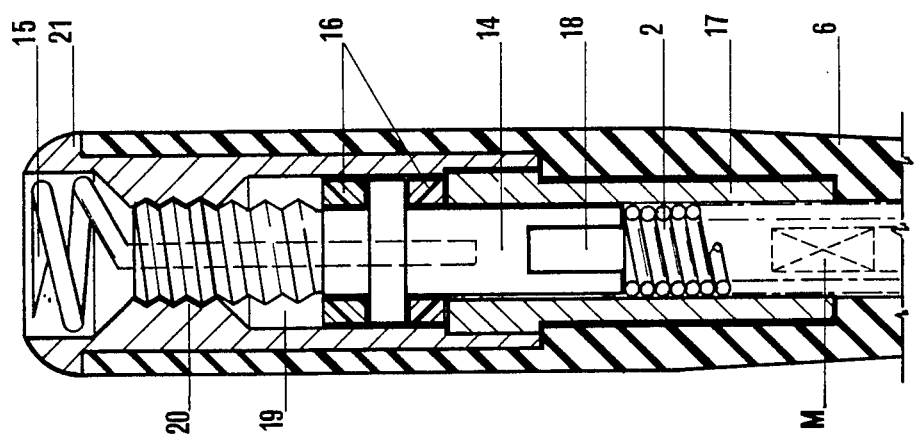

Referring to FIG. 5, the auricular electrode 4 consists of a body 7, preferably in platinum-iridium alloy (though any conductive bio-compatible material possessing resistance to chemical and electrolytic corrosion might be used), of moving parts 8 and 9, an encapsulation cylinder 10, ring seals 11, and an insulation tube 12.

Parts 8, 9 and 10 are embodied in the same material as the body 7 (Pt-Ir alloy in the example described), whereas the seals 11 are preferably in silicon rubber (or in polyurethane or other similar bio-compatible material), and the insulation tube 12 in nylon or Delrin or other bio-compatible plastic.

To implant the electro-catheter, the stylet is worked from the end denoted E such that its key end engages a socket 13 in the cylindrical moving part 8. Axial rotation thus imparted to the part 8, to which the spiral hook 9 is either soldered or crimped, turns the hook from the stowed position (FIG. 2a), about the axis of moving part 8, into an opened-out position (FIG. 2b) wherein the sharp point projects from the electrode in such a way as to permit of engaging the cardiac muscle tissue, and the body 7 of the electrode is brought into ample surface contact with the heart wall.

The seals 11 disallow infiltration of organic fluids (principally blood) between the breasted surfaces of the body 7 and the pivoted moving part 8 and onto the spiral-wound conductor 3. The encapsulation cylinder 10 is either soldered or crimped to the body 7 of the elctrode, and that part of the cylinder which projects from body 7 provides a union to which the dual-core catheter sheath 1 may be made fast.

The same applies in the case of the insulation tube 12 through which the spiral-wound conductor denoted 2 passes through the body 7 without making any electrical contact: that part of the tube 12 which projects from the body 7 at the spiral hook end serves as a union to which the thin single-core ventricular catheter sheath 6 may be made fast. The conductor 2 in question extends down to the distal electrode 5, the ventricular, and is either soldered or crimped thereto.

With reference to FIG. 4, the ventricular electrode consists of a body 21 housing a threaded pin 14 the function of which is to support the spiral anchor 15 and cause it to project from the electrode 5. The spiral anchor is either soldered or crimped to the pin 14, and the pin itself is shaped in such a way as to shift rotatingly through the cavity 19 provided in the electrode by turning in a female thread 20 offered by the body 21. Rotational movement is produced by a stylet M having a distal key embodied such as to register with a corresponding socket 18 in the relative moving part, i.e. the threaded pin 14. The ventricle stylet, like that of the atrium, consists of a length of straightened stainless steel wire.

Protection of the electrode assembly 21 ... 14 against infiltration of organic fluids is ensured by two ring seals 16 of a flexible and bio-compatible material (preferably silicon rubber).

A sleeve 17 soldered or crimped to the electrode body 21, provides for proximal encapsulation of the spiral anchor mechanism; the proximal extremity of the sleeve itself provides a union to which the conductor 2 may be soldered or crimped. FIG. 4 shows the electrode 5 with anchor retracted, the state in which it is inserted through the vena cava and into the ventricle.

Once positioned in the ventricle, rotation of the stylet M causes the spiral anchor to project and 'corkscrew' into the cardiac muscle, thus ensuring mechanical fixture and electrical contact.

With reference to FIG. 3, positioning of the electro-catheter in the cardiac chambers is accomplished as follows: intravenous insertion comes about as with an ordinary ventricular catheter; with the ventricular stylet inserted, the ventricle electrode is maneuvered into position within the ventricular chamber, and anchored by turning the stylet so as to corkscrew the spiral metal anchor 15 in a clockwise direction (as viewed in FIG. 4).

This stylet is removed, and the atrial stylet slipped into the bore of the relative spiral-wound conductor 3. The catheter must now be urged further into the atrium until the electrode makes contact with the wall; contact is made to best effect in the upper-middle region, and in any event should be such that the electrical signal from the atrium is as strong as possible, and the stimulation threshold as low as possible. At this point, turning the stylet clockwise (as viewed in FIG. 2a) will open out the spiral hook 9, whereupon turning counter-clockwise (as viewed in FIG. 2b) will cause it to engage the cardiac muscle of the atrium. This done, the stylet is removed, and the electrode remains in position, securely anchored mechanically, and making efficient electrical contact.

Anchored thus, the electrodes can be wired up to advantage with any artificial pacemaker of the following implantable types: V.A.T. (synchronization of ventricular stimulus utilizing an atrial signal); D.V.I. (sequential auriculo-ventricular stimulation with ventricular inhibition); D.D.D. (sequential stimulation of the two chambers, with the option of utilizing atrial and ventricular signals for pacemaking purposes); and in fact all those models of pacemaker requiring electrode-implant in the atrium and/or ventricle.

In a preferred embodiment of the electro-catheter, the stretch of conductor 2 and surrounding sheath 6 immediately following the auricular electrode might be pre-formed to create a permanent though flexibly adjustable bend, which would facilitate location of the electrode 4 against the atrium wall and maintain its position thereagainst during implantation.

What is claimed is:

1. An electro-catheter for physiological cardiac stimulation, which comprises:

a first flexible insulating sheath formed of a bio-compatible material, the first sheath having first and second parallel bores formed longitudinally therethrough;

a second flexible insulating sheath formed of a bio-compatible material, the second sheath having a third bore formed longitudinally therethrough, the third bore of the second sheath being in communication with the first bore of the first sheath;

first and second conductors, each conductor being spirally wound to define an internal bore, the first conductor being received by the first bore of the first sheath and the third bore of the second sheath, the second conductor being received by the second bore of the first sheath;

a first electrode, the first electrode being electrically connected to the second conductor and mounted near one end of the first sheath for placement in the atrium of a patient;

a second electrode, the second electrode being electrically connected to the first conductor and mounted near one end of the second sheath for placement in the ventricle of the patient; and first anchoring means mounted on the first electrode for anchoring the first electrode to a muscle wall of the atrium, the first anchoring means including a spiral hook of conductive bio-compatible material, the spiral hook including a free end having a sharpened point, and means for pivoting the spiral hook radially with respect to the second sheath from a first position, wherein the hook is partially wrapped around the second sheath in close contact to the periphery thereof, to a second position, wherein the hook extends outwardly from the second sheath to expose the pointed free end thereof.

2. An electro-catheter as defined by claim 1, which further comprises:

a first stylet having a key-shaped end, the stylet being received within the internal bore of the second conductor and being adapted to rotate therein; and wherein the spiral hook of the first anchoring means includes a socket end disposed opposite the pointed free end, the socket end being dimensioned to closely receive the key-shaped end of the stylet wherein rotation of the stylet causes the spiral hook to pivot between the first and second position.

3. An electro-catheter as defined by claim 2, which further comprises:

an insulation tube, the insulation tube being disposed between the first electrode and the first conductor, the insulation being formed from a bio-compatible material.

4. An electro-catheter as defined by claim 3, which further comprises:

second anchoring means connected to the first conductor for anchoring the second electrode to a muscle wall of the ventricle, the second anchoring means including a corkscrew shaped hook formed of conductive bio-compatible material and having a pointed free end, the hook being adapted to rotate to engage the ventricle muscle wall.

5. An electro-catheter as defined by claim 4, which further comprises:

means defining a bore for receiving the corkscrew-shaped hook, the bore defining means being situated at one end of the second sheath; and wherein the corkscrew-shaped hook of the second anchoring means is adapted to be movable in a first position, wherein it is entirely housed by the bore defining means, and a second position, wherein it is partially exposed from the bore defining means; and wherein the catheter further comprises a second stylet having a key-shaped end, the second stylet being received by the internal bore of the first conductor and being adapted to rotate therein; and wherein the corkscrew hook of the second anchoring means includes a socket end opposite the pointed end, the socket end being dimensioned to closely received the key-shaped end of the second stylet wherein rotation of the second stylet causes the corkscrew-shaped hook to move between the first position and the second position.

6. An electro-catheter as defined by claim 3, wherein the second sheath and the first conductor are formed with an adjustable bend such that the catheter will maintain the position of the first electrode against the muscle wall of the atrium during implantation of the catheter.

* * * * *